United States Patent
Litzenberg et al.

(10) Patent No.: US 7,553,321 B2
(45) Date of Patent: Jun. 30, 2009

(54) CHEMICALLY BASED VASCULAR OCCLUSION DEVICE DEPLOYMENT

(75) Inventors: Marc W. Litzenberg, Miami Shores, FL (US); Donald K. Jones, Lauderhill, FL (US); Vladimir Mitelberg, Aventura, FL (US)

(73) Assignee: Cordis Development Corporation, Miami Lakes, FL (US)

( * ) Notice: Subject to any disclaimer, the term of this patent is extended or adjusted under 35 U.S.C. 154(b) by 550 days.

(21) Appl. No.: 11/394,876

(22) Filed: Mar. 31, 2006

(65) Prior Publication Data

US 2007/0239192 A1    Oct. 11, 2007

(51) Int. Cl.
  *A61F 2/06*  (2006.01)
  *A61M 29/00*  (2006.01)

(52) U.S. Cl. ..................... 623/1.1; 606/200

(58) Field of Classification Search .......... 606/200, 606/108, 213; 623/1.11
See application file for complete search history.

(56) References Cited

U.S. PATENT DOCUMENTS

| | | | |
|---|---|---|---|
| 5,002,556 A | | 3/1991 | Ishida et al. |
| 5,108,407 A | | 4/1992 | Geremia et al. |
| 5,609,608 A | | 3/1997 | Benett et al. |
| 5,637,087 A | | 6/1997 | O'Neil et al. |
| 5,989,242 A | | 11/1999 | Saadat et al. |
| 6,063,100 A | | 5/2000 | Diaz et al. |
| 6,068,644 A | | 5/2000 | Lulo et al. |
| 6,117,142 A | * | 9/2000 | Goodson et al. ............ 606/108 |
| 6,238,415 B1 | * | 5/2001 | Sepetka et al. ............ 606/213 |
| 6,254,612 B1 | * | 7/2001 | Hieshima ............ 606/108 |
| 6,277,125 B1 | * | 8/2001 | Barry et al. ............ 606/108 |
| 6,478,773 B1 | | 11/2002 | Gahndi et al. |
| 6,494,884 B2 | | 12/2002 | Gifford, III et al. |
| 6,581,324 B1 | | 6/2003 | Creeger et al. |
| 6,641,576 B1 | | 11/2003 | Vito et al. |
| 6,689,141 B2 | * | 2/2004 | Ferrera et al. ............ 606/108 |
| 6,743,236 B2 | | 6/2004 | Barry et al. |
| 6,871,594 B1 | | 3/2005 | Estrella |
| 6,958,068 B2 | * | 10/2005 | Hieshima ............ 606/108 |
| 2003/0220666 A1 | | 11/2003 | Mirigian et al. |
| 2004/0153025 A1 | | 8/2004 | Seifert et al. |
| 2004/0218966 A1 | | 11/2004 | Fuller |
| 2004/0225279 A1 | | 11/2004 | Raymond |

FOREIGN PATENT DOCUMENTS

| | | |
|---|---|---|
| EP | 1537838 | 12/1995 |
| WO | WO 92/09651 | 6/1992 |

* cited by examiner

*Primary Examiner*—Vy Q Bui
(74) *Attorney, Agent, or Firm*—Michael W. Montgomery

(57) ABSTRACT

A vascular occlusion device deployment system for placing an occlusion device at a preselected site within the vasculature of a patient. The deployment system employing a pusher having a lumen with an opening at the distal end of the pusher. A vascular occlusion device is connected to the distal end of the pusher by a portion that is removeably disposed within the opening. The portion of the occlusion device is forced out of the opening by an expandable reaction chamber, thereby deploying the occlusion device. The expandable reaction chamber, prior to deployment, has multiple chambers separated by a heat-dissolvable membrane. When the membrane is dissolved, components from the chambers react and expand, leading to deployment.

13 Claims, 3 Drawing Sheets

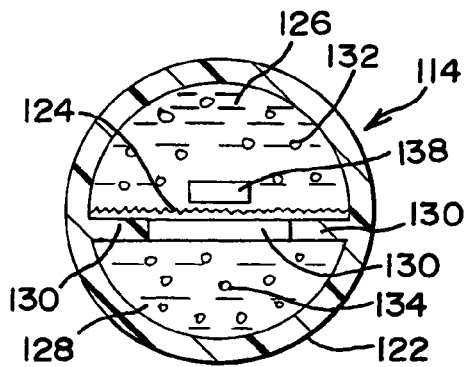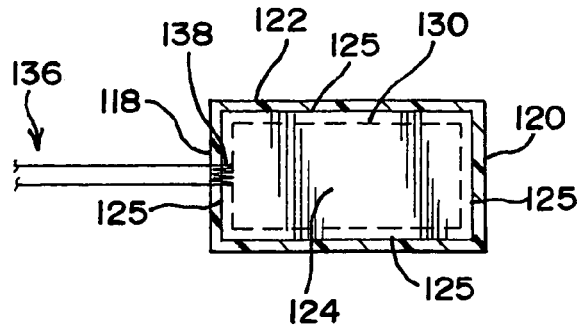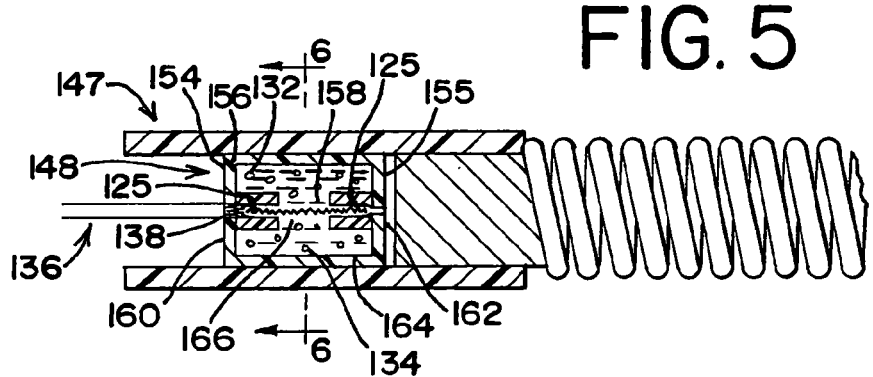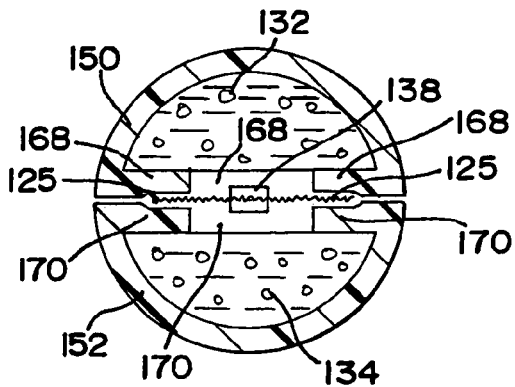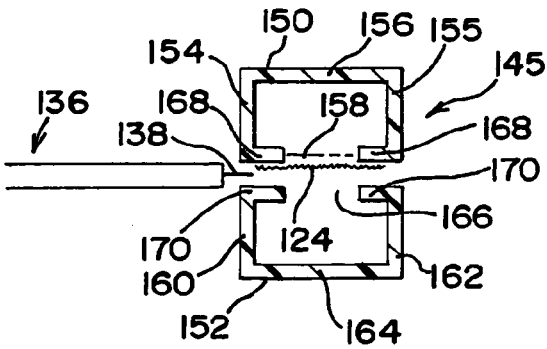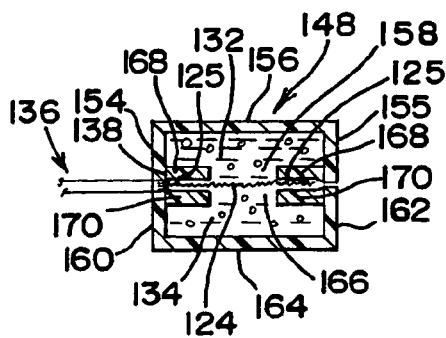

CHEMICALLY BASED VASCULAR OCCLUSION DEVICE DEPLOYMENT

FIELD OF THE INVENTION

The present invention is related to deployment systems and methods for accurately and rapidly deploying vascular occlusion devices at a preselected location within the vascular system of a patient, and more particularly, deployment approaches that utilize an expanding chemical reaction chamber to facilitate rapid deployment of vascular occlusion devices.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat such a defect. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has been delivered by the catheter and provides a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transmits the light into heat energy. The heat energy raises the temperature of the connector and opens the fingers, thereby releasing the embolic coil. This patent, and all other patents and references identified herein are hereby incorporated herein by reference.

SUMMARY OF INVENTION

The present invention embodies a deployment system and method for accurately and rapidly deploying a vascular occlusion device at a preselected site within the vasculature of a patient. The deployment system may employ an elongated flexible delivery catheter for guiding a deployment unit to the preselected site. The deployment unit includes a delivery tube or pusher that pushes and guides the vascular occlusion device, such as an embolic coil, through the delivery catheter to the preselected site.

The pusher may include an internal lumen which has an opening at the distal end of the pusher. The occlusion device includes a portion, such as a headpiece, which is removeably disposed within the opening by a friction fit between the headpiece and the inner surface of the pusher. This arrangement maintains the connection between the occlusion device and the deployment unit until the desired deployment.

A reaction chamber is positioned within the lumen of the pusher. The reaction chamber includes an expandable wall adjacent the headpiece of the occlusion device. The reaction chamber also includes two reactants which are separated by a heat dissolvable membrane. When the heat dissolvable membrane dissolves, the reactants mix within the chamber to create a product that expands to a volume greater than the original reactants. The product pushes against the expandable wall of the chamber which in turn contacts the headpiece. The force of the expandable wall against the headpiece overcomes the fictional force between the headpiece and the inner wall of the lumen, forcing the headpiece out of the opening, thereby deploying the vascular occlusion device.

In another embodiment the pusher has a gripper located at a distal end portion of the pusher. The gripper has an expandable gripping element for releasably attaching a vascular occlusion device to the deployment system. In this embodiment, the reaction chamber operatively communicates with the gripper. When the reaction chamber expands, it applies force to the gripper to cause the gripper to expand outwardly and release the occlusion device.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 3 is a cross-sectional view of the reaction chamber of the deployment unit shown in FIG. 2 taken along line 3-3;

FIG. 4 is a cross-sectional view of the reaction chamber of the deployment unit shown in FIG. 2 taken along line 4-4;

FIG. 5 is an enlarged partially sectioned view of another embodiment of a deployment unit of the present invention;

FIG. 6 is a cross-sectional view of the reaction chamber of the deployment unit shown in FIG. 5 taken along line 6-6;

FIG. 7 is an exploded view of the reaction chamber and heating element of the deployment unit shown in FIG. 5;

FIG. 8 is a cross-sectional view of the reaction chamber and heating element of the deployment unit shown in FIG. 5;

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
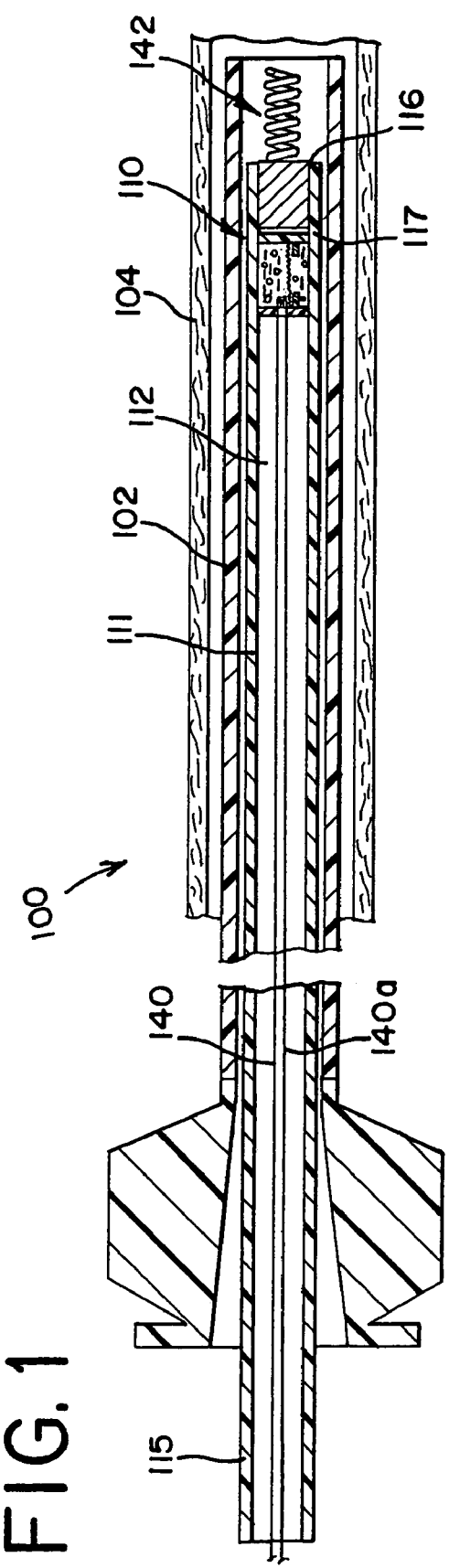
FIG. 1 is an enlarged partially sectioned view of a vascular occlusion device deployment system of the present invention.

FIG. 1 generally illustrates a preferred embodiment of the vascular occlusion device deployment system of the present invention. The deployment system, generally designated at 100, includes an elongated flexible guiding catheter 102 which is inserted into the vasculature of a patient, such as blood vessel 104, and used to guide a deployment unit, generally designed 110, to a preselected site in a manner generally known in the art. The deployment unit 110 includes an elongated flexible pusher or delivery tube 111 having a proximal end portion 115 and a distal end portion 117. An internal lumen 112 extends from the proximal end portion 115 to the distal end portion 117 of the pusher 111. A vascular occlusion device 142, generally illustrated as an embolic coil, is removeably disposed within an opening 116 (which can be seen in FIG. 9) of the lumen 112 at the distal end 117 of the pusher 111.

Figure 2:
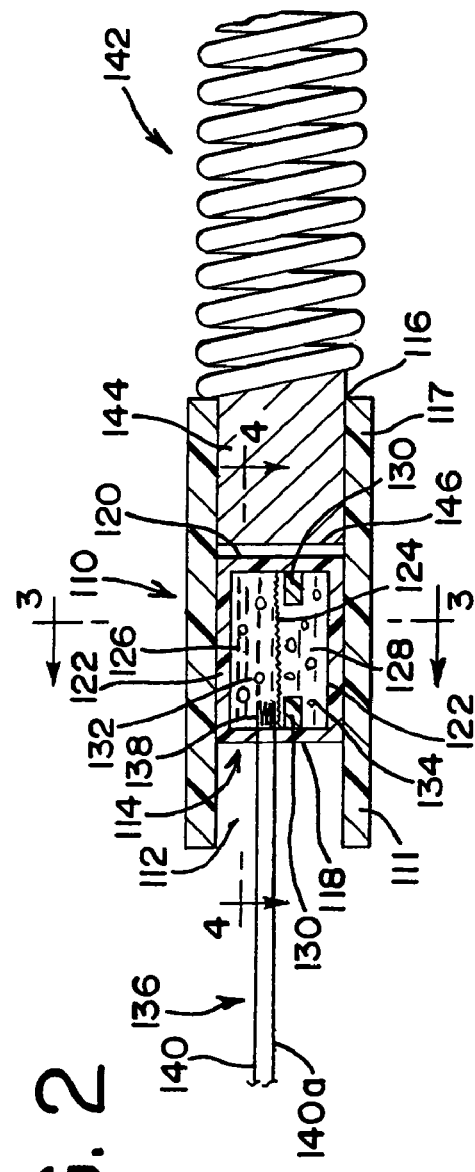
FIG. 2 is an enlarged partially sectioned view of an embodiment of a deployment unit of the present invention.

FIG. 2 illustrates one embodiment of the delivery unit. The delivery unit 110 includes a reaction chamber 114 located within the lumen 112 proximal the opening 116 in the distal end portion 117 of the pusher 111. Illustratively, the reaction chamber 114 has a generally cylindrical shape (as shown in FIG. 3) that is defined by a proximal wall 118, a distal wall 120 and a continuous sidewall 122 located between the proximal wall and distal wall. It will be understood that the reaction chamber can be a shape other than cylindrical, for example, a square defined by the appropriately shaped walls.

The distal wall 120 is comprised of an elastic expandable member. Preferably, the distal wall 120 is a membrane made of a silicone elastomer having substantial flexibility and elasticity. The proximal wall 118 and sidewall 122 also can be membranes made of a silicone polymer. The materials used in forming the proximal wall 118, distal wall 120 and sidewall 122 should be selected as not to significantly degrade when exposed to heat or while in contact with the reactants. Typically, the respective membranes will have different Durometer hardness values. For example, the proximal wall 118 and sidewall 122 are preferably made of a higher Durometer polymer than the distal wall 120.

A heat dissolvable membrane 124 is positioned within the reaction chamber 114 to separate the reaction chamber into a first compartment or sub-chamber 126 and a second compartment or sub-chamber 128. The heat dissolving membrane is preferably made from a material that will not significantly degrade when in contact with the reactants, and readily dissolves in the presence of heat energy. Typical membrane materials include polyolefins such as polyethylene, copolymers and various blends.

The heat dissolvable membrane preferably degrades at a temperature above body temperature, and more preferably above a temperature of at least about 40 degrees C., most preferably above at least about 42 degrees C. When used herein in this context, the term degrades indicates that the membrane will fail to maintain separation between the respective compartments that it separates before this membrane thus degrades and allows the respective materials in the respective compartments to contact one another.

In the illustrated embodiment, the reaction chamber 114 includes a lip or ridge 130 that extends circumferentially around the perimeter of the inside of the reaction chamber. As illustrated in FIG. 4, the marginal edges 125 of the heat dissolvable membrane 124 are attached to the lip 130 (partially shown in phantom) by, for example, a biocompatible adhesive.

Referring back to FIGS. 2 and 3, a first reactant 132 is housed within the first sub-chamber 126, and a second reactant 134 is housed within the second sub-chamber 128. When the first reactant 132 and the second reactant 134 are combined, they produce a product that has a greater volume than the combined volume of the first and second reactants prior to combining.

The first and second reactants 132, 134 can be any reactants that produce a product having a greater volume than the original compositions. Preferably, the first and second reactants may be any of the reactants disclosed in Cooke et al., WO 92/09651, hereby incorporated herein by reference, which produce a polycyanoacrylate foam. In particular, the first reactant is preferably a mixture of cyanoacrylate monomer and ethanol and the second reactant is preferably a mixture of ethanol and N,N-Dimethyl-p-toluidine. Other reactant materials that when combined form a foam material with an increased bulk volume relative to the reactants, such as precursors for polyurethane foam are also suitable. Additionally, the material of the heat dissolving membrane and the reactants should be chosen so that the reactants do not significantly degrade the membrane and that the membrane does not significantly affect the properties of the reactants.

In one method of assembling the reaction chamber 114, the reaction chamber can be assembled, and then the first and second reactants 132, 134 can be injected into their respective sub-chambers 126, 128 by piercing a needle through an appropriate wall of the reaction chamber and injecting the reactant. When assembling the reaction chamber 114 in this fashion, the walls through which the reactants are injected must be sufficiently elastic to recover after the needle has been removed to prevent leakage.

As shown in FIG. 2, a heat generating system 136 extends through the proximal wall 118 of the reaction chamber and into the reaction chamber 114. The heat generating system 136 includes a heating element 138, for example an electrical resistance heating coil that is attached to a set of leads 140, 140a extending through the lumen 112. Referring to FIG. 3, the heating element 138 is positioned within the chamber so that when heat energy radiates from the heating element, the heat energy activates or dissolves the heat dissolvable membrane 124. Preferably, the heating element 138 is in contact with the heat dissolvable membrane 124.

When the heating element 138 is an electrical resistance heating coil, the temperature of the heating element can be elevated by supplying electrical current from a power source (not shown) to the heating element via the leads 140, 140a. In an alternative embodiment, the heat generating system 136 can comprise a fiber optic cable that has a heating element located at a distal end portion of the fiber optic cable, as disclosed in pending U.S. application Ser. No. 11/171,898, filed Jun. 30, 2005, hereby incorporated herein by reference. In this alternative embodiment, light energy, preferably laser-light energy, is transmitted through the fiber optic cable to the heating element. The heating element absorbs the light energy causing it to increase in temperature.

Referring to FIG. 2, the illustrated vascular occlusion device 142 includes a portion or headpiece 144 which is sized and shaped to be removeably disposed within the opening 116 at the distal end 117 of the pusher 111 so that a proximal end 146 of the headpiece 144 is adjacent the distal wall 120 of the chamber 114. The headpiece 144 is preferably held in place by a friction fit with the inner surface of the pusher 111 until the desired time of deployment, as will be discussed herein. Alternatively, the headpiece 144 may by held in place by a relatively weak biocompatible adhesive or by any other suitable manner.

As stated above, the occlusion device 142 may be an embolic coil which may take various forms and configurations, and may also be filled with a fibrous material or maybe coated with a beneficial substance, such as a biogel to promote clotting. Alternatively, the occlusion device also may be any other occlusive device or approach known in the art such as hydrogels, foams, bioactive coils, braids, cables and hybrid devices.

Another embodiment of the delivery unit is illustrated in FIGS. 5-8. The delivery unit 147 of this embodiment is generally similar to the previous embodiment except that the reaction chamber 148 is of a different construction. As illustrated in FIG. 7, the reaction chamber 148 is comprised of two discrete sections, namely a first sub-chamber 150 and a second sub-chamber 152. Referring to FIG. 6, illustratively, the reaction chamber is cylindrically shaped, and the first and second sub-chambers 150, 152 are semi-cylindrically shaped in cross-section. Turning to FIGS. 5, 7 and 8, the first sub-chamber 150 includes a proximal wall 154, a distal wall 155 and a sidewall 156 between the proximal wall and distal wall. The first sub-chamber also includes an opening 158. Likewise, the second sub-chamber 152 includes a proximal wall 160, a distal wall 162 and a sidewall 164. The second sub-chamber 152 also includes an opening 166. The first sub-chamber 150 includes a lip 168 that extends around the perimeter of the opening 158. The second sub-chamber 152 also includes a lip 170 that extends around the perimeter of the opening 166.

The distal wall 155 of the first sub-chamber 150 and the distal wall 162 of the second sub-chamber 152 are comprised of an elastic expandable membrane. The proximal walls 154, 160 and the sidewalls 156, 164 of the first and second chamber 150, 152 are preferably made from a higher Durometer polymer and are more rigid than the distal walls 155, 162.

Referring to FIGS. 5, 6 and 8, the first sub-chamber 150 and the second sub-chamber 152 are attached together at the lips 168, 170 so that the opening 158 of the first sub-chamber 150 is generally aligned with the opening 166 of the second sub-chamber 152, at least such that the openings open into each other. The sub-chambers 150, 152 are preferably attached together by an adhesive, but can also be attached by any other suitable method known in the art, such as melt or heat bonding.

A heat dissolvable membrane 124 is positioned between the opening 158 of the first sub-chamber 150 and the opening 166 of the second sub-chamber 152. The heat dissolvable membrane 124 prevents communication between the first sub-chamber 150 and the second sub-chamber 152 until the membrane is dissolved. The dissolvable membrane 124 is held in position by attaching the membrane to the first sub-chamber 150, the second sub-chamber 152 or both the first and second sub-chambers. Preferably, the marginal edges 125 of the heat dissolvable membrane 124 are sandwiched between the lips 168, 170 of the first and second sub-chambers 150, 152 and attached, such as by an adhesive, as illustrated in FIGS. 5, 6 and 8.

As illustrated in FIG. 6, a first reactant 132 is housed within the first sub-chamber 150, and a second reactant 134 is housed within the second sub-chamber 152. When the first reactant 132 and the second reactant 134 are combined, they produce a product that has a greater volume than the combined volume of the first and second reactants prior to combining. The first and second reactants can be the same reactants as described above or any other reactants that produce a product that has a greater volume than the combined volume of the first and second reactants.

The delivery unit 147 includes a heat generating system 136, generally similar to the heat generating system described above. The heat generating system 136 includes a heating element 138 positioned between the first and second sub-chambers 150, 152. The heating element 138 is situated so that when the heating element is activated, heat energy radiating from the heating element dissolves the heat dissolvable membrane 124.

Referring to FIG. 7, in one method of assembling the reaction chamber 148, the first sub-chamber 150 can be filled with the first reactant and then the heat dissolvable membrane can be adhered to the lip 168 of the first sub-chamber. The second sub-chamber 152 can be filled with the second reactant. The first sub-chamber 150 and the second sub-chamber 152 can then be adhered together to form the reaction chamber 148 with the heating element 138 fitting between the first sub-chamber and the second sub-chamber.

Figure 9:
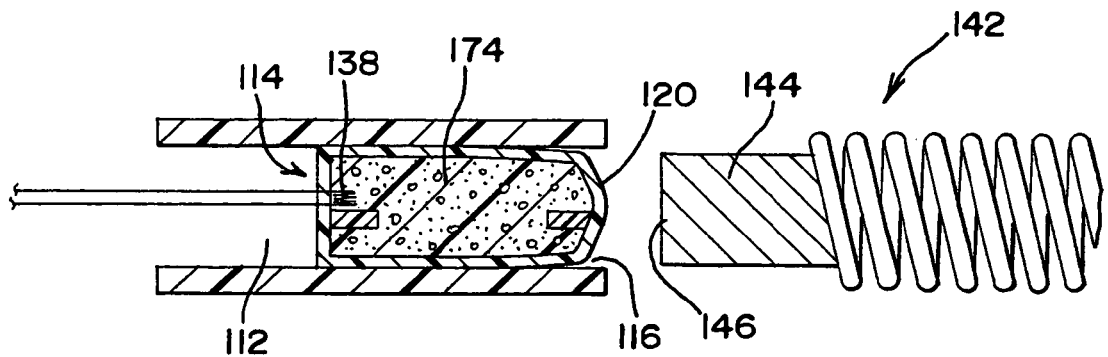
FIG. 9 is an enlarged partially sectioned view of the deployment unit of FIG. 2 shown just after deployment of the occlusion device.

The operation of the delivery units 110 and 147 shown in FIGS. 2 and 5, respectively, will generally be described in relation to FIGS. 1, 2 and 9. A catheter 102 is inserted into the vasculature of the patient, such as blood vessel 104, and positioned at a preselected location, typically in conjunction with other devices and professional procedures as generally known in the art. The delivery unit 110 is inserted into and advanced through the catheter 102. Once the delivery unit 110 reaches the desired location, the delivery unit 110 is advanced and/or the catheter 102 is moved in a retrograde manner such that the delivery unit moves with respect to and within the catheter until the occlusion device 142 moves through the catheter 102 and out of the distal end of the catheter.

During the procedure and before the occlusion device 142 has been deployed, if it is determined that the distal end of the catheter 102 or the occlusion device 142 is not in the correct location, the occlusion device 142 may be retrieved back into the distal end of the catheter by retracting the delivery unit 110 proximally or advancing the catheter distally. Once the occlusion device as been retrieved, the catheter and/or the occlusion device 142 may be repositioned.

When the occlusion device 142 is in the correct position, the heating element 138 is activated, for example, by activating the power source when using an electrical resistance coil or by transmitting laser-light energy through a fiber optic cable when a light energy absorbable heating element is used. After activation, the temperature of the heating element 138 rises and the heating element radiates or releases heat energy. The heat energy causes the heat dissolvable membrane 124 to dissolve which in turn allows the first and second reactants 132, 134 to combine to form a product 174. Referring to FIG. 9, the product 174 has a greater volume than the combined volume of the first and second reactants 132, 134 prior to reacting. The expanding volume of the product 174 forces the lower durometer distal wall 120 of the reaction chamber 114 to expand or stretch distally within the lumen 112, contacting the proximal end 146 of the headpiece 144 and forcing the headpiece out of the opening 116, thereby deploying the occlusion device 142.

Figure 10:
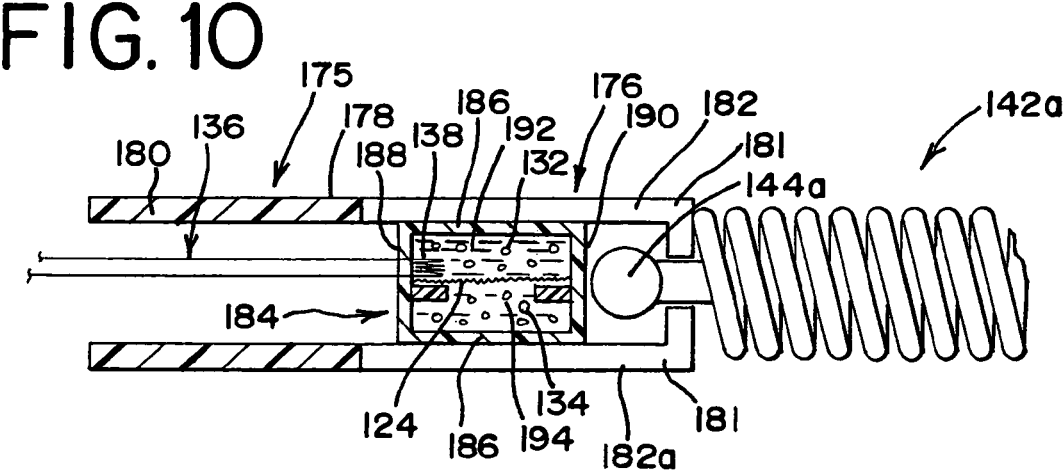
FIG. 10 is an enlarged partially sectioned view showing another embodiment of a deployment unit of the present invention.
Figure 11:
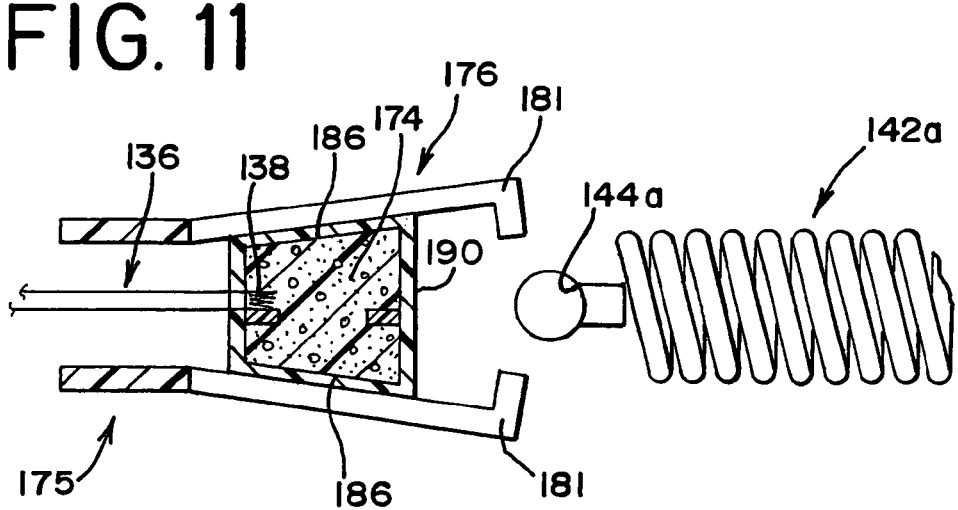
FIG. 11 is an enlarged partially sectioned view of the deployment unit of FIG. 10 shown just after deployment of the occlusion device.

FIGS. 10 and 11 illustrate yet another embodiment of the present invention. In this embodiment, the delivery unit 175 includes a gripper 176 similar to the gripper disclosed in co-pending U.S. application Ser. No. 11/171,897, filed Jun. 30, 2005, hereby incorporated herein by reference. The gripper 176 is located at the distal end portion 178 of the pusher 180. The gripper 176 includes an outwardly expandable gripping element 181, which is generally illustrated as a plurality of jaws 182, 182a. The gripping element 181 releasably engages a protruding portion or headpiece 144a of vascular occlusion device 142a. As will be discussed in more detail below, when the gripping element 181 expands outwardly, it releases the headpiece 144a of the occlusion device 142a.

The gripper 176 may be comprised of polymer, such as FEP Teflon, PTFE Teflon, polyvinyl chloride, a polyolefin or a neoprene, or any other suitable polymer, and may be constructed as disclosed in Bennett et al. U.S. Pat. No. 5,609,608, hereby incorporated herein by reference. Alternatively, the gripper 176 may be constructed of any suitable metal, or the gripper could comprise a microtube which has been slit. A suitable microtube may be made of stainless steel or of a nickel-titanium alloy such as Nitinol, or other suitable material. Further, in the illustrated embodiment, the gripper 176 is a separate unit which is attached to the pusher 180 in any suitable manner, for example by a silicone or cyanoacrylate adhesive. However, it is also contemplated that the gripper 176 and pusher 180 could be a unitary structure.

An expandable reaction chamber 184, similar to the expandable reaction chambers 114 or 148 of the previous embodiments, is positioned at least partially within the gripper 176. In this embodiment, the sidewall 186 of the reaction chamber 184 has a lower Durometer value than the proximal wall 188 and distal wall 190.

Referring to FIG. 10, similar to the reaction chamber of the previous embodiments, the reaction chamber includes a first sub-chamber 192 and a second sub-chamber 194 separated by a heat dissolvable membrane 124. The first sub-chamber 192 contains a first reactant 132, and the second sub-chamber 194 includes a second reactant 134, similar to the reactants described above. The delivery unit 175 also includes a heat generating system 136 to dissolve the heat dissolving membrane.

When the heat dissolvable membrane 124 is dissolved, the first and second reactants 132, 134 are mixed to produce a product 174 which has a greater volume than the combined volume of the first and second reactants prior to mixing, as illustrated in FIG. 11. The expanding product 174 pushes against the inner surface of sidewall 186, causing the sidewall 186 to outwardly expand. The force of the expanded sidewall 186 against the gripping element 181 forces the gripping element to outwardly expand or open. Movement in this regard can be in a generally radial direction. Optionally, the distal wall 190 can have a Durometer value which allows it to expand to contact the headpiece 144a of the occlusion device 142a and push the headpiece 144a out of and away from the expanded gripping element 181, when this action is desired.

In operation, a catheter 102 is inserted into the vasculature system of a patient and positioned at a preselected location within a blood vessel 104, typically in conjunction with other devices and professional procedures as generally known in the art. Using the methods described above, the delivery unit 175 is inserted into and advanced through the catheter 102 to place the occlusion device 142a at a desired location within the blood vessel.

During the procedure and before the occlusion device 142a has been deployed, if it is determined that the distal end of the catheter 102 or the occlusion device is not in the correct location, the occlusion device may be retrieved back into the distal end of the catheter by retracting the delivery unit proximally or advancing the catheter distally. Once the occlusion device 142a has been retrieved, the catheter 102 and/or the occlusion device may be repositioned.

When the occlusion device 142a is in the correct position, the heating element 138 is activated to dissolve the heat dissolvable membrane. The first and second reactants 132, 134 mix and react to produce product 174 which has a larger volume than the combined volumes of the first and second reactants prior to mixing, as illustrated in FIG. 11. The expanding product 174 pushes against the inner wall of the sidewall 186 of the reaction chamber 184, causing the sidewall to expand. The expanded sidewall 186 presses against the gripping element 181 outwardly expanding or opening the gripping element to release the occlusion device 142a at the preselected location within the blood vessel. If desired, the distal wall 190 may simultaneously press against the headpiece 144a to push it out of and away from the gripping element 181, thereby deploying the vascular occlusion device 142a.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion deployment system, comprising:
a deployment unit comprising a pusher having a proximal end portion and a distal end portion with a distal opening,
the distal opening sized and shaped to temporarily accept a protruding portion of a vascular occlusion device;

an expandable reaction chamber located within the pusher proximal the distal opening of the pusher, the expandable chamber expandable in a direction toward the distal end portion of the pusher;

said reaction chamber including a first sub-chamber and a second sub-chamber separated by a heat dissolvable membrane;

a first reactant located within the first sub-chamber and a second reactant located within the second sub-chamber;

a heating generating system capable of dissolving the heat dissolvable element to allow said first reactant and second reactant to mix, forming a product that expands in the direction of the distal opening; and said expanding product applying a force to the reaction chamber causing a portion of the reaction chamber to expand in the direction of the distal opening, said portion of the reaction chamber capable of contacting a protruding portion of a vascular occlusion device within the distal opening and pushing the protruding portion out of the distal opening, thereby deploying the vascular occlusion device.

2. The deployment system of claim 1, wherein the heat dissolvable membrane is of a material that comprises a polyolefin.

3. The deployment system of claim 1, wherein the heat dissolvable membrane degrades at a temperature above human body temperature.

4. The deployment system of claim 3, wherein said temperature is at least about 40 degrees C.

5. The deployment system of claim 1, wherein the first reactant comprises a mixture of cyanoacrylate monomer and ethanol, and the second reactant comprises mixture of ethanol and N,N-Dimethyl-p-toluidine.

6. The deployment system of claim 1, wherein the product comprises a polycyanoacrylate foam.

7. The deployment system of claim 1, wherein the reaction chamber comprises a polymeric material.

8. The deployment system of claim 1, wherein the heat generating system comprises an electrical resistance heating coil connected to a power source via electrical leads.

9. The deployment system of claim 1, wherein the vascular occlusion device is an embolic coil.

10. The deployment system of claim 1, wherein the first sub-chamber and second sub-chamber are discrete sections.

11. A method for deployment of a vascular occlusion device at a preselected location within the vasculature of a patient, comprising:

providing a deployment unit comprising a pusher member having a distal end opening and a reaction chamber proximal thereof, said chamber including a first sub-chamber and a second sub-chamber separated by a heat dissolvable membrane, a first reactant housed in said first sub-chamber and a second reactant housed in the second sub-chamber;

removably disposing a vascular occlusion device having a portion protruding into the distal end opening of the lumen;

using the deployment unit to place the vascular occlusion device at a preselected location within the vasculature of a patient;

dissolving the heat dissolving membrane to cause the first reactant and the second reactant to react within the chamber, said reactants producing a product which has a larger volume than the reactants; and directing the expanding product toward the distal end opening to remove the protruding portion from the distal end opening of the lumen, thereby deploying the vascular occlusion device.

12. The method according to claim 11, wherein said dissolving the heat dissolving membrane comprises dissolving the heat dissolving membrane with an electrical resistance heating coil.

13. The method according to claim 11, wherein said first reactant comprises a mixture of cyanoacrylate monomer and ethanol, and the second reactant comprises mixture of ethanol and N,N-Dimethyl-p-toluidine.

* * * * *